United States Patent [19]

Czech et al.

[11] Patent Number: 5,189,065
[45] Date of Patent: Feb. 23, 1993

[54] USE OF DERIVATIVES OF 9,10-DIHYDROPHENANTHRENE FOR THE PREPARATION OF AN ANTI-TUMOR MEDICAMENT

[75] Inventors: Jorg Czech; Hans H. Sedlacek, both of Marburg, Fed. Rep. of Germany; Lucien Nedelec, Le Raincy, France; Jacques Guillaume, Paris, France; Christian Marchandeau, Annet S/Marne, France

[73] Assignee: Roussel Uclaf, Paris, France

[21] Appl. No.: 752,467

[22] PCT Filed: Dec. 27, 1990

[86] PCT No.: PCT/FR90/00952
§ 371 Date: Oct. 17, 1991
§ 102(e) Date: Oct. 17, 1991

[87] PCT Pub. No.: WO91/09833
PCT Pub. Date: Jul. 11, 1991

[30] Foreign Application Priority Data

Dec. 28, 1989 [FR] France .................... 89 17302

[51] Int. Cl.$^5$ .......................................... A61K 31/135
[52] U.S. Cl. .............................. 514/656; 514/231.2; 514/255; 514/325; 514/385; 514/401; 514/403; 514/429; 514/617; 514/629; 514/654; 514/655; 544/155; 544/381; 546/203; 546/204; 548/300.1; 548/347.1; 548/356.1; 548/529; 564/184; 564/222; 564/427; 564/374; 564/384
[58] Field of Search ............... 564/184, 222, 374, 384, 564/427; 514/617, 629, 656, 654, 655, 231.2, 255, 325, 385, 401, 403, 429

[56] References Cited

PUBLICATIONS

Freedman et al., Br. J. Pharm., vol. 67 (1979) pp. 143–152.
Petterson et al., J. Computer-Aided Molecular Design, No. 1 (1987) pp. 143–152.
Yasuda et al., J. Chem. Soc., No. 5 (May 1988) pp. 745–751.
Cannon et al., J. Med. Chem., vol. 18 (1975) pp. 108–110.
Nichols et al., J. Med. Chem. vol. 21 (1978) pp. 395–398.
Yasuda et al., J. Org. Chem., vol. 52 (1987) pp. 753–759.

*Primary Examiner*—Richard L. Raymond
*Attorney, Agent, or Firm*—Bierman and Muserlian

[57] ABSTRACT

The use of products of formula (I) is described, wherein X and Y represent hydrogen, hydroxy or alkoxy; and $R_1$ and $R_2$ represent H, alkyl, alkenyl or alkynyl, arylalkyl, acyl or $R_1$ and $R_2$ together with nitrogen form a heterocycle for preparing an antitumoral drug.

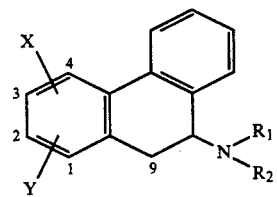

(I)

4 Claims, No Drawings

USE OF DERIVATIVES OF 9,10-DIHYDROPHENANTHRENE FOR THE PREPARATION OF AN ANTI-TUMOR MEDICAMENT

The invention relates to the use of derivatives of 9,10-dihydrophenanthrene for the preparation of an anti-tumor medicament and notably of an anti-cancer medicament, the use as medicaments of derivatives of 9,10-dihydrophenanthrene and products derived from this structure The expression of oncogenes in a cell of a mammal leads to the transformation of types of normal cells into cancerous cells. Said transformation is caused by the infection of a cell by a retrovirus. There can be cited as a well-known example, the infection of hens by the Rous virus which leads to the appearance of a cancer. The corresponding oncogene which is responsible for the malignant transformation was named "SRC" gene (J. S. Grugge RL Erikson, Nature 269, 346-348 (1977).

Many oncogenes known up until now, are characterized by the expression of a protein possessing a kinase activity. These enzymes catalyse the transfer of the terminal phosphate group of ATP onto an amino acid. Contrary to many of the other proteinkinases which transfer the phosphate group onto a seryl or threonyl remainder, the majority of oncogene kinases phosphorylize a tyrosyl remainder of the protein chain. Moreover it is known that the oncogene products, namely those of v-mos, v-mil and v-raf oncogenes have a specific serine/threonine proteinkinase activity (K. Rolling et al., Nature (London) 312, 558-561 (1984), B. Singh et al., Journal of Virology 60, 1149-1152 (1986).

The tyrosinekinase activity plays an integral part in the function of certain growth factor receptors. New results show that the growth of many tumors depends on the presence of growth factors such as Epidermal Growth Factor (EGF), the "Transforming Growth Factor Alpha (TGFAlpha) or the "Platelet Derived Growth Factor" (PDGF) (A. S. Goustin, G. D. Shipley, H. L. Moses, Cancer Research 46, 1015-1029 (1986). As a consequence of the link between the growth factor and its receptor, the tyrosinekinase, which is a specific component of the growth factor receptor, is stimulated.

Therefore it is to be expected that an inhibitor of tyrosinekinase and also of serine/threoninekinase can inhibit the growth and the proliferation of tumors and can be used in anti-tumor therapy.

It has just been discovered, in a surprising fashion, that the products of formula (I) as defined hereafter are oncogene kinases inhibitors such as tyrosinekinase, serine/threoninekinase and tyrosinekinase of the growth factor receptor and are thus of use in the treatment of tumor-related illnesses. The products of formula (I) which have anti-proliferative, anti-oncotic and carcinostatic properties can, in particular, be used to inhibit the growth and proliferation of tumors and in tumor therapy.

Therefore a subject of the present invention is the use of products of general formula I):

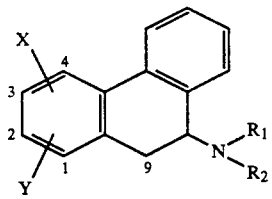

in which X and Y, identical of different, are chosen from hydrogen atoms and hydroxy radicals and alkyloxy radicals having 1 to 4 carbon atoms and $R_1$ and $R_2$, identical or different, are chosen from hydrogen atoms, alkyl, alkenyl or alkynyl radicals having at most 4 carbon atoms, arylalkyl and acyl radicals, or $R_1$ and $R_2$ from together with the nitrogen atom to which they are linked a heterocycle with five or six links capable of carrying an optionally substituted second heteroatom chosen from nitrogen, oxygen or sulphur atoms, as well as their addition salts with mineral or organic acids for the preparation of an anti-tumor medicament.

Among the values of X and Y there can be mentioned in addition to the hydrogen and hydroxy values, the following radicals: methoxy, ethoxy, propyloxy, isopropyloxy, butyloxy, sec-butyloxy, isobutyloxy, tert-butyloxy. The hydroxy value is preferred.

Among the values of $R_1$ and $R_2$, there can be mentioned in addition to the hydrogen values, the following radicals:
methyl, ethyl, propyl, isopropyl, butyl, isobutyl, secbutyl, tert-butyl,
vinyl, allyl, propenyl,
ethynyl, propargyl, 1-propynyl, 3-butynyl,
benzyl, phenylethyl,
formyl, acetyl, propionyl, benzoyl.

$R_1$ and $R_2$ can also form with the nitrogen atom to which they are linked, the following radicals: pyrrolidinyl, imidazolinyl, imidazolidinyl, pyrazolidinyl, piperidinyl, morpholinyl, piperazinyl, methylpiperazinyl, ethylpiperazinyl or propylpiperazinyl.

The addition salts with mineral or organic acids can be, for example, the salts formed with the following acids: hydrochloric, hydrobromic, nitric, sulphuric, phosphoric, acetic, formic, propionic, malonic, maleic, fumaric, succinic, tartaric, citric, oxalic, glyoxalic, aspartic, alkanesulphonic, such as methane- or ethanesulphonic acids, arenesulphonic, such as benzene- or paratoluene sulphonic acids and arylcarboxylic, such as benzoic acids. The preferred salts are hydrochlorides, hydrobromides and acetates.

The medicaments which are subjects of the present invention can be presented in the form of pharmaceutical compositions intended for administration by digestive, parenteral or local route. They can be prescribed in the form of plain or sugar-coated tablets, capsules, granules, suppositories, injectable preparations, ointments, creams, gels, which are prepared according to the usual methods.

The active ingredient or ingredients can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The dosage varies as a function of the affection to be treated and the administration route, for example, it can vary from 10 to 500 mg per day for an adult by oral route, Preferably the dose used can be from 50 to 250 mg per day by oral route.

In particular a subject of the invention is the use of the products of formula (I$_a$):

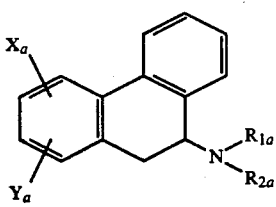

(I$_a$)

in which X$_a$ and Y$_a$ are such that either they each represent a hydroxy radical, or one represents a hydroxy radical and the other a hydrogen atom, R$_{1a}$ and R$_{2a}$ are chosen from the alkyl radicals having from 1 to 4 carbon atoms, preferably methyl and the acyl radicals, preferably formyl, acetyl or benzoyl, as well as their addition salts with mineral or organic acids, preferably hydrochlorides, hydrobromides and acetates, for the preparation of an anti-tumor medicament.

More particularly a subject of the invention is the use of one of the following products:
3,4-dihydroxy-9-methylamino-9,10-dihydrophenanthrene,
3,4-dihydroxy-9-dimethylamino-9,10-dihydrophenanthrene, and their addition salts with mineral or organic acids, for the preparation of an anti-tumor medicament.

Also a subject of the invention is, as medicaments, the products of general formula (I'):

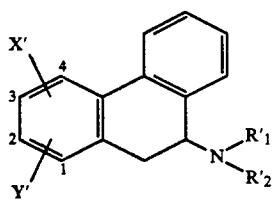

(I')

in which X' and Y', identical or different, are chosen from hydrogen atoms and hydroxy and alkyloxy radicals having 1 to 4 carbon atoms and R'$_1$ and R'$_2$, identical or different, are chosen from hydrogen atoms, alkyl, alkenyl or alkynyl radicals having at most 4 carbon atoms, arylalkyl and acyl radicals, or R'$_1$ and R'$_2$ form together with the nitrogen atom to which they are linked a heterocycle with five or six links being able to carry a second optionally substituted heteroatom chosen from nitrogen, oxygen or sulphur atoms, it being understood that:
a) when X' and Y' each represent a hydroxy radical in positions 3 and 4, R'$_1$ and R'$_2$ cannot each represent a methyl radical,
b) when X' and Y' each represent a hydroxy or methoxy radical in positions 2 and 3, R'$_1$ and R'$_2$ cannot each represent a hydrogen atom,
c) when X' and Y' each represent a methoxy radical in positions 2 and 3, R'$_1$ and R'$_2$ cannot represent one of them a hydrogen atom and the other a benzoyl radical, as well as the addition salts with mineral or organic acids.

Particularly a subject of the invention is, as a medicament, 3,4-dihydroxy-9-methylamino-9,10-dihydrophenanthrene and its addition salts with mineral or organic acids.

Also a subject of the invention is the pharmaceutical compositions containing as active ingredient at least one of the medicaments defined above.

The pharmaceutical compositions which are a subject of the invention can be prepared as indicated above.

Also a subject of the invention is the products of general formula (I''):

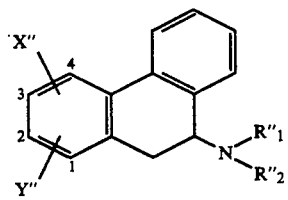

(I'')

in which X'' and Y'', identical or different, are chosen from hydrogen atoms and hydroxy and alkoxy radicals having 1 to 4 carbon atoms and R''$_1$ and R''$_2$, identical or different, are chosen from hydrogen atoms, alkyl, alkenyl or alkynyl radicals having at most 4 carbon atoms, arylalkyl and acyl radicals, or R''$_1$ and R''$_2$ form together with the nitrogen atom to which they are linked a heterocycle with five or six links being able to carry a second optionally substituted heteroatom chosen from nitrogen, oxygen or sulphur atoms, it being understood that:
a) when X'' and Y'' each represent a hydroxyl or methoxy radical in positions 3 and 4, R''$_1$ and R''$_2$ cannot each represent a methyl radical,
b) when X'' and Y'' each represent a methoxy radical in positions 3 and 4, R''$_1$ and R''$_2$ cannot each represent a hydrogen atom,
c) when X'' and Y'' each represent a hydroxy or methoxy radical in positions 2 and 3, R''$_1$ and R''$_2$ cannot each represent a hydrogen atom,
d) when X'' and Y'' each represent a methoxy radical in positions 2 and 3, R''$_1$ and R''$_2$ cannot represent one of them a hydrogen atom and the other a benzoyl radical,
e) when X'' and Y'' each represent a hydrogen atom, R''$_1$ and R''$_2$ are such that:
 i) R''$_1$ and R''$_2$ cannot each represent a hydrogen atom or a methyl or ethyl radical,
 ii) one of R''$_1$ and R''$_2$ cannot represent a hydrogen atom when the other represents one of the following radicals: methyl, ethyl, allyl, isopropyl, tert-butyl, benzyl or phenylethyl,
as well as their addition salts with mineral or organic acids.

More particularly a subject of the invention is the product of formula (I'') as defined above and corresponding to the following formula: - 3,4-dihydroxy-9-methylamino-9,10-dihydrophenanthrene and its addition salts with mineral or organic acids.

The products of formula (I'') are new products. The products of formulae (I) and (I') are known and can be prepared by processes described in the literature.

Notably the following references can be mentioned:
J. Comput-Aided Mol. Des. (1987) 1(2), 143-152

J. Med. Chem. (1975), 18(1), 108-110
J. Med. Chem. (1978), 21(4), 395-8
Br. J. Pharmacol. (1979), 67(3), 430P-431P
J. Org. Chem. (1987), 52(5), 753-9
J. Org. Chem. (1985), 50(19), 3667-9
J. Pharm. Pharmacol. (1983), 35(12), 780-5
Zh. Org. Khim, (1983) 19(7), 1552-3

A preparation method for the products of formula (I″) is shown hereafter and forms part of the subject of the invention.

Also a subject of the invention is a preparation process for the products of formula (I″) as defined above characterized in that on a product of formula (I″$_a$):

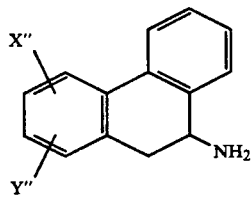

(I″$_a$)

in which X″ and Y″ have the meaning indicated above, either to prepare a product of formula (I″$_b$) corresponding to a product of formula (I″) in which one of R″$_1$ and R″$_2$ is different from hydrogen and the other represents a hydrogen atom, is reacted with either an equivalent of a product of formula R$_{12}$Hal in which R$_{12}$ represents the R″$_1$ or R″$_2$ radical and Hal represents a halogen atom,
or an equivalent of a product of formula

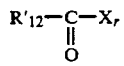

in which R′$_{12}$ represents the R″$_1$ or R″$_2$ radical in which a carbon atom has been removed and X$_r$ represents a reactive group, and the product obtained is optionally subjected to a reduction, or to prepare a product of formula (I″$_c$) corresponding to a product of formula (I″) in which R″$_1$ and R″$_2$ are identical and do not represent a hydrogen atom, is reated with either two equivalents of a product of formula R$_{12}$Hal in which R$_{12}$ and Hal have the previous meaning, or two equivalents of a product of formula

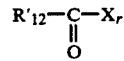

in which R′$_{12}$ and X$_r$ have the previous meaning and the product obtained is optionally subjected to a reduction, or to prepare a product of formula (I″$_d$) corresponding to a product of formula (I″) in which R″$_1$ and R″$_2$ are different and do not represent a hydrogen atom, is reacted with either an equivalent of a product of formula R$_1$Hal followed by an equivalent of a product of formula R$_2$Hal, or an equivalent of a product of formula

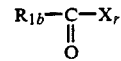

in which R$_{1b}$ represents the R″$_1$ radical in which a carbon atom has been removed followed by either an equivalent of a product of formula R$_2$Hal, or an equivalent of a product of formula

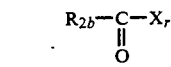

in which R$_{2b}$ represents the R″$_2$ radical in which a carbon atom has been removed and that in the two cases the product obtained is optionally subjected to a reduction, or to prepare a product of formula (I″$_e$) corresponding to a product of formula (I″) in which R″$_1$ and R″$_2$ form together with the nitrogen atom to which they are linked a heteroatom with five or six links being able to carry an optionally substituted second heteroatom chosen from nitrogen, oxygen or sulphur, is reacted with either a product of formula:

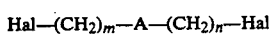

in which m and n are integers different from zero chosen in such a way that their sum is equal to 3 or 4 and A represents a methylene radical, a sulphur, oxygen or nitrogen atom, optionally substituted, or a product of formula:

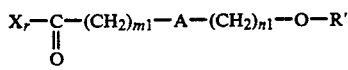

in which X$_r$ and A have the previous meaning, m1 and n1 are integers different from zero chosen in such a way that their sum is equal to 2 or 3 and R′ represents a protector group of the hydroxyl radical, the product obtained is subjected to a deprotection reaction of said hydroxyl radical then said hydroxyl radical is converted either into a halogen atom or a reactive derivative, then one or other of the products obtained is subjected to a cyclization reaction and finally to a reduction reaction, and if desired the products of formula (I″) obtained in which at least one of X″ or Y″ represents an alkyloxy radical are converted by hydrolysis into a corresponding product in which X″ and Y″ represent a hydroxy radical and if desired the products of formula (I″) are converted into their mineral or organic acid salts.

In a preferred method of implementing the above process, the halogen atom which can be represented by Hal is preferably a bromine atom, but Hal can also represent a chlorine or iodine atom.

The addition of the product of formula R$_{12}$Hal onto the product of formula (I″$_a$) as well as the addition of equivalent halogenated products (R$_{12}$Hal or R$_2$Hal) is carried out in the usual conditions, thus the operation preferably takes place in the presence of a base such as soda, potash or a basic salt such as sodium carbonate.

The addition of the product of formula

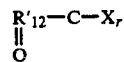

or the equivalent products

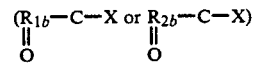

is also carried out in the usual amidification conditions. The reactive group which can be represented by $X_r$ can be a halogen atom or the remainder of an acyl group so that

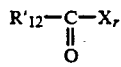

represents a symmetrical or mixed anhydride or an activated ester. Therefore, for example, the mixed formyl acetic anhydride can be used. Also known amidification methods can be used such as the addition of an ester onto the amine in the presence of trialkylaluminium. The reduction which is optionally carried out on the products obtained is also carried out in the usual conditions. For example, a hydride is used such as lithium aluminium hydride or a borane such as the ($BH_3$, $Me_2S$) complex. When $R_{12}$ represents a hydrogen atom, the operation can also take place in the presence of formic acid so as to directly obtain the product of formula ($I''_b$) in which one of $R''_1$ or $R''_2$ represents a methyl radical.

When a product of formula:

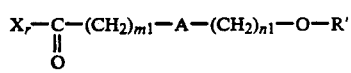

is added, the protector group which is represented by R' can be for example, a tetrahydropyrannyl radical or a tert-butyl, trimethylsilyl or another trialkylsilyl radical.

The elimination of this group is carried out in the usual conditions such as acid hydrolysis using a mineral or organic acid such as hydrochloric acid or sulphuric acid.

The exchange reaction of the hydroxyl radical by a hydrogen atom is also carried out in the usual conditions such as the action of thionyl chloride. The reactive derivative of the hydroxyl which can be used can be the tosylate or the mesylate prepared in the usual way. The cyclization reaction is carried out in the conditions indicated above, for the addition of halides such as $R_{12}Hal$.

The hydrolysis of the substituents X" and/or Y" when at least one of these substituents represents an alkoxy radical is preferably carried out in an acid medium. For example hydrochloric acid or preferably hydrobromic acid is used.

The salification of the products of formula (I") is carried out according to the usual methods. The operation then is preferably carried out using one of the acids mentioned above.

The products of formula ($I''_a$) can be prepared as follows: an acid of formula (II):

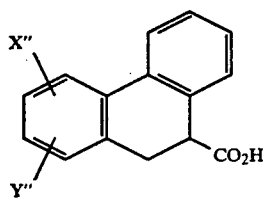
(II)

in which X" and Y" have the meaning indicated above is esterified by the usual methods so as to obtain a product of formula (III):

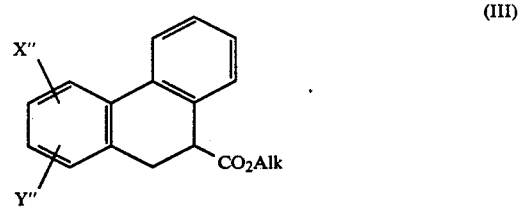
(III)

in which Alk represents an alkyl radical having 1 to 4 carbon atoms, on which product hydrazine is reacted in order to obtain the product of formula (IV):

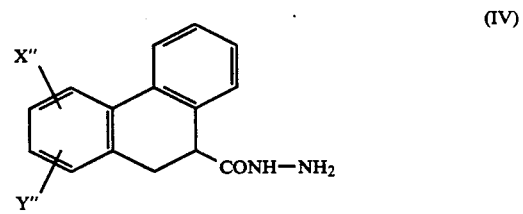
(IV)

which is treated with a nitrite then an alkanol in order to obtain the product of formula (V):

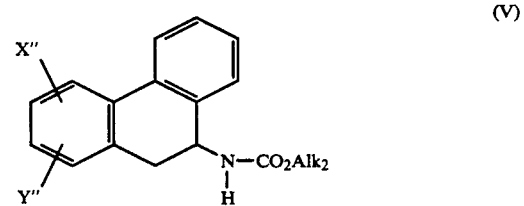
(V)

in which $Alk_2$ represents an alkyl radical having 1 to 4 carbon atoms, which product is treated with a base in order to obtain the expected product of formula ($I''_a$).

In a preferred method of executing this process:
a) X" and Y" do not represent a free OH radical but rather a hydrogen atom or an alkoxy radical,
b) the esterification is carried out either by diazoalkane such as diazomethane or in the presence of an alkanol such as ethanol,
c) the formation of the hydrazine of formula (IV) is carried out using hydrazine hydrate in ethanol under reflux,
d) the change of products of formula (IV) to products of formula (V) is carried out according to the technique described in the reference J. Am. Chem. Soc. (1947) 69, 1998. An aqueous solution of sodium nitrite in acetic acid is used to obtain the acylazide which is converted in situ, under the action of an alkanol such as ethanol under reflux, into the expected product. $Alk_2$ preferably represents an ethyl radical.
e) The saponification of the products of formula (V) into products of formula ($I''_a$) is preferably carried out using alcoholic potash or soda. An acidification can then take place for example using a hydrohalic acid such as hydrochloric or hydrobromic acid in order to obtain the salt, the corresponding hydrochloride or hydrobromide. Such a reaction is found in J. Med. Chem. (9175), 18(1), 108–10.

The products of formula (II) can themselves be prepared as follows: phenylacetic acid or a salt of this acid is reacted on a product of formula (VII):

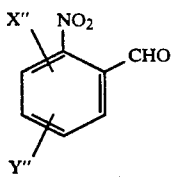

in order to obtain a product of formula (VIII):

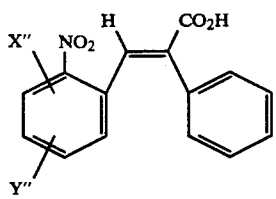

which is subjected to a reduction in order to obtain a product of formula (IX):

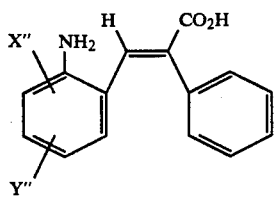

which is subjected to a cyclization agent in order to obtain a product of formula (X):

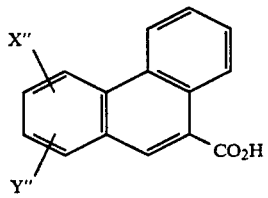

which is subjected to a reduction agent in order to obtain the expected product of formula (II).

In a preferred method of inplementing this preparation:

a) a phenylacetic acid salt is used such as the sodium salt. The reaction is carried out in the presence of acetic anhydride,
b) the reduction of the product of formula (VIII) into the product of formula (IX) is carried out in the presence of ferrous sulphate in ammonia water whilst heating (Ber. 33, 1810, (1900), J. Am. Chem. Soc. 69, 1998, (1947)),
c) the cyclization of the products of formula (IX) is carried out in dilute sulphuric acid in the presence of sodium nitrite then of copper prepared extemporaneously from copper sulphate,
d) the final reduction is preferably carried out using a sodium amalgam at about 4% on the sodium salt of the product of formula (X) in solution in aqueous soda and acidification then takes place using hydrochloric acid (Helv. Chem. Acta. 31, 1119–1132, (1948)),
e) the reaction chain is preferably carried out on a product of formula (VII) in which X" and Y" do not represent a hydroxy radical, that is to say either a hydrogen atom or an alkoxy radical.

The nitrobenzaldehydes of formula (VII) can in their turn be prepared as follows: a nitration is carried out, preferably using nitric acid for example in carbon tetrachloride, on a product of formula (XII):

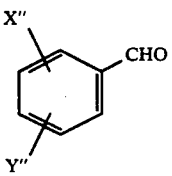

One can start for example with products in which X" and Y" are in the protected form such as a hydroxy radical acylated for example by an acetyl radical.

Numerous references will be found in the literature describing the preparation of the products of formula (VII) for example:

J. Med. Chem. (1987), vol. 30(2) p. 303–18
J. Med. Chem. (1974), vol. 17(10) p. 1086–90
Can. J. Chem. (1978), vol. 56(21) p. 2725–30
Org. Chem. (1984) vol 49(7) p. 1238–46
EP 0,173,349 (European Patent)
J. Med. Chem. (1987), vol. 30(2) p. 295–303
DE 2,905,054 (German Patent)
Chim. Ther. (1970), vol. 5(4) p. 274–8
J. Heterocycl. Chem. (1973), vol. 10(4) p. 649–54
J. Heterocycl. Chem. (1986), vol. 23(6) p. 1805–14
EP 0,028,473
Acta. Pharm. Suec, (1979), vol. 16(1) p. 64–73
J. Indian. Chem. Soc. (1969), vol. 46(7) p. 651–5
U.S. Pat. No. 4,044,134 (American Patent)
Ann. Chim. (Rome), (1970), vol. 60(10–11) p. 688–96
Synth. Commun. (1986), vol. 16(6) p.681–7
Tetrahedron, (1978), vol. 34(15) p.2355–9
Farmaco. Ed.Sci, (1972), vol. 27(9) p. 731–43
U.S. Pat. No. 4,595,765
J. Heterocycl. Chem. (1987), vol. 24(4) p. 941–3
DE 3,707,088
EP 0,188,094
J. Indian Chem. Soc. (1969), vol. 46(1) p. 31–8
J. Med. Chem. (1986), vol. 29(8) p. 1239–40
Monatsh. Chem. 68, vol. 99(6) p. 2349–58
U.S. Pat. No. 4,672,116
J. Heterocycl. Chem. (1986), vol. 23(6) p. 1821–8

The preparations for the products of formula (VII) can also be found in Beilsteins.

EXAMPLE 1

3,4-dimethoxy-9-formamido-9,10-dihydrophenanthrene

A solution of 2.2 g of formylacetic anhydride in 20 cm³ of benzene is added to a solution of 4.53 g of 9-amino-3,4-dimethoxy-9,10-dihydrophenanthrene (described in J. Med. Chem. 1975, 18(1), 108-10) in 20 cm³ of anhydrous benzene. After one hour of agitation at ambient temperature the whole is poured into a saturated solution of sodium bicarbonate. Ethyl acetate is added followed by decanting, washing with water and with salt water, drying over magnesium sulphate and evaporating to dryness. 4.8 g of crystallized product is obtained which melts at 139° C.

The product is redissolved in 25 cm$^3$ of ethyl acetate under reflux. Crystallization is started, the whole is allowed to cool down and is then chilled for two hours. After filtering and rinsing with ethyl acetate, 3.556 g of expected product is obtained. M.p. = 139°-140° C.

By evaporating the mother liquors 1.2 g of crystallized product is obtained which is taken up in a benzene-ethyl acetate (7:3) mixture then chromatographed on silica (eluant: benzene - ethyl acetate (7:3)) and an extra 656 mg of product is obtained (M.p. = 144°-145° C.), making 4.21 g of product in total.

An analytical specimen is obtained by recrystallizing 100 mg of product from ethyl acetate under reflux. In this way 69 mg of purified product is obtained. M.p. = 144°-145° C.

IR Spectrum (CHCl$_3$)
NH at 3428 cm$^{-1}$
Carbonyl complex 1688-1683 cm$^{-1}$
Aromatic regions + NH deformations 1495 cm$^{-1}$
UV Spectrum
Infl. 230 nm $E'_1$ = 693 epsilon = 19600
Infl. 260 nm $E'_1$ = 524
Max. 268 nm $E'_1$ = 635 epsilon = 18000
Infl. 277 nm $E'_1$ = 473
Infl 298 nm $E'_1$ = 87 epsilon = 2460

EXAMPLE 2

3,4-dimethoxy-9-methylamino-9,10-dihydrophenanthrene (hydrochloride)

A solution of 5.35 g of aluminium chloride in 30 m$^3$ of anhydrous tetrahydrofuran is added over 20 minutes to a suspension of 1.54 g of lithium aluminium hydride in 70 cm$^3$ of anhydrous tetrahydrofuran. Agitation takes place for 15 minutes then 3.834 g of 3,4-dimethoxy-9-formamido-9,10-dihydrophenanthrene obtained in Example 1 in suspension in 30 cm$^3$ of tetrahydrofuran is. Agitation takes place for 5 and a half hours.

The whole is poured into iced water which has had soda added to it, ethyl acetate is added, followed by agitation and filtering. After decanting, washing with water then salt water and drying over magnesium sulphate, the solvents are evaporated off.

3.7 g of resin is obtained which is taken up in ethyl acetate with 3% triethylamine and chromatographed on silica eluting with the same mixture.

3.31 g of 3,4-dimethoxy-9-methylamino-9,10-dihydrophenanthrene is collected in the form of a resin.

The hydrochloride is obtained by operating as follows: the resin is dissolved in 10 cm$^3$ of ethyl acetate and ethyl acetate saturated with hydrochloride gas is added until a pH of 1 is reached. The hydrochloride crystallizes out. The whole is left under agitation for one hour then evaporated to dryness. 3.6 g of hydrochloride is obtained. M.p. = about 265° C.

An analytical sample is obtained by dissolving 200 mg of hydrochloride in 2 cm$^3$ of ethanol. After filtering whilst hot and allowing to cool, crystallization is started followed by chilling for one hour. After filtering and rinsing, 69 mg of purified product is obtained. M.p. = 265° C.

IR Spectrum (CHCl$_3$)
Aromatics 1606-1572 cm$^{-1}$
Aromatics + NH$_2$ deformations 1495 cm$^{-1}$
Absorption region OH, NH.

UV Spectrum (EtOH) Infl. 230 nm $E'_1$ = 540 Max. 269 nm $E'_1$ = 564 epsilon - 17200 Infl. 290 nm $E'_1$ = 172 Infl 305 nm $E'_1$ = 75

EXAMPLE 3

3,4-dihydroxy-9-methylamino-9,10-dihydrophenanthrene (hydrobromide)

3.4 g of 3,4-dimethoxy-9-methylamino-9,10-dihydrophenanthrene hydrochloride obtained in Example 2 in 25 cm$^3$ of 66% hydrobromic acid is heated under reflux for one hour under nitrogen.

The crystallized product is allowed to cool down and is filtered under vacuum. After rinsing with isopropanol and drying in the presence of P$_2$O$_5$, 3.157 g of expected 3,4-dihydroxy-9-methylamino-9,10-dihydrophenanthrene hydrobromide is obtained. M.p. = 245° C.

The product is redissolved in 20 cm$^3$ of ethanol under reflux, followed by filtering whilst hot, concentrating to one half until crystallization and allowing to cool. After filtering and rinsing with ethanol, 1.737 g of purified product is obtained. M.p. = 245° C.

IR Spectrum (nujol)
Aromatic + NH$_2$ deformation = 1632 cm$^{-1}$, 1600 cm$^{-1}$
1578 cm$^{-1}$, 1509 cm$^{-1}$
NH region, absorption associated OH at 3162 cm$^{-1}$
UV Spectrum (ethanol) Infl. 216 nm $E'_1$ = 855 Infl 270 nm $E'_1$ = 468 Max. 274 nm $E'_1$ = 502 epsilon = 16200 Infl 285 nm $E'_1$ = 343 Max. 313,5 nm $E'_1$ = 115 epsilon = 3700

PHARMACOLOGICAL TESTS

1 - Measurement of the Inhibition of Tyrosinekinase of the EGF (Epidermal Growth Factor) Receptor Membranes of A431 cells (ATCC CRL 1555) are used as the source of EGF receptors. This cellular lineage expresses a large number of EGF receptors at its surface which have a tyrosinekinase activity.

These cells are pre-incubated with or without EGF (1000 nM) for 15 minutes and are added to a corresponding HEPES buffer (N-2-hydroxyethyl-piperazine-N'-2-ethanesulphonic acid) (with or without EGP) and containing Mg$^{2+}$ (10 mM) and Mn$^{2+}$ (2 mM) ions, 0.2% of X-100 triton, sodium orthovanadate (20 micromoles) and the inhibitor.

Samples either containing or not containing the poly substrate (Glu, Ala, Tyr 6:3:1) are prepared. The reaction is initiated by the addition of [gamma P$^{32}$] ATP (32 micromoles). After incubation for 15 minutes at 30° C. the samples are precipitated using 10% chloroacetic acid, followed by filtering on a millipore membrane and the incorporated P$^{32}$ is measured with a liquid scintillation counter.

The results are expressed in IC$_{50}$, that is the concentration of substance which inhibits the enzyme activity by 50%, determined by a series of dilutions starting at 51 micrograms/ml in the samples containing the substrate and EGF.

The following results are obtained:
Product A: 0.6 micrograms/ml.
Product of Example 3: 0.2 micrograms/ml.

2 - Measurement of the Inhibition of the Proteinkinase Dependent on Cyclic 3',5'-AMP The catalytic sub-unit of the proteinkinase dependent on cyclic 3',5'-AMP was reconstituted as indicated in SIGMA ®. The enzyme activity was measured using KEMPTID ® (SIGMA ®) as substrate (KEMPTID - Leu-Arg-Arg-Ala-Ser-Leu-Gly).

The inhibitor is pre-incubated at pH 6.9 with the enzyme, the substrate (190 micromoles), $Mg^{+2}$ (5 mM), 0.25 mg/ml of BSA (Bovine Serum Albumin) and 3.75 mM of mercaptoethanol in 50 mM of 4-morpholinopropanesulphonic acid.

The reaction is initiated using gamma $P^{32}$ ATP (40 micromoles). After 15 minutes at 30° C. an aliquot is placed on an ion-exchange paper ($2 \times 2$ cm$^3$; WHATMAN ®) plunged into phosphoric acid (75 mM), washed, dried and the incorporation of $P^{32}$ is measured using a liquid scintillation counter.

The results are expressed as a percentage of the enzyme activity inhibition at a concentration of inhibitor of 40 micrograms/ml.

The following results are obtained:

Product A: 19%

Product of Example 3: 18%

In the above tests, product A is 3,4-dihydroxy-9-dimethylamino-9,10-dihydrophenanthrene described in J. Med. Chem. 1975, 18(1) 108–10.

We claim:

1. A method of treating tumors in warm-blooded animals comprising administering to warm-blooded animals an antitumorally effective amount of at least one member of the group consisting of a compound of the formula

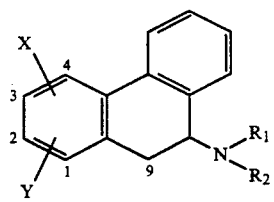

I wherein X and Y are individually selected from the group consisting of hydrogen, —OH and alkoxy of 1 to 4 carbon atoms, $R_1$ and $R_2$ are individually selected from the group consisting of hydrogen, alkyl of 1 to 4 carbon atoms, alkenyl and alkynyl of 2 to 4 carbon atoms, aralkyl and acyl or taken together with the nitrogen to which they are attached from a 5- or 6- member heterocycle optionally containing a second heteroatom selected from the group consisting of nitrogen, sulfur and oxygen and their non-toxic, pharmaceutically acceptable acid addition salts.

2. The method of claim 1 wherein the active compound has the formula

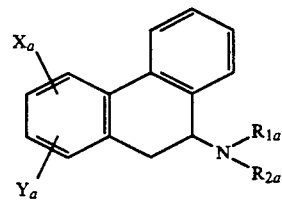

I$_a$ wherein $X_a$ and $Y_a$ are both —OH or one is —OH and the other is hydrogen and $R_{1a}$ and $R_{2a}$ are alkyl of 1 to 4 carbon atoms or acyl.

3. The method of claim 2 wherein $R_{1a}$ and $R_{2a}$ are selected from the group consisting of methyl, formyl, acetyl and benzoyl.

4. The method of claim 1 wherein the compound is selected from the group consisting of 3,4-dihydroxy-9-methylamino-9,10-dihydrophenanthrene and 3,4-dihydroxy-9-dimethylamino-9,10-dihydrophenanthrene and their non-toxic, pharmaceutically acceptable acid addition salts.

* * * * *